United States Patent [19]
Saiga et al.

[11] Patent Number: 5,243,989
[45] Date of Patent: Sep. 14, 1993

[54] ULTRASONIC IMAGING DEVICE WITH NOISE PREVENTING STRUCTURE

[75] Inventors: Kazuya Saiga, Hachioji; Masashi Abe, Hino; Hiroshi Fujimoto, Hachioji, all of Japan

[73] Assignee: Olympus Optical Co., Ltd., Tokyo, Japan

[21] Appl. No.: 686,028

[22] Filed: Apr. 16, 1991

[30] Foreign Application Priority Data

May 11, 1990 [JP] Japan .................................. 2-122097
Jul. 24, 1990 [JP] Japan .................................. 2-195914

[51] Int. Cl.$^5$ .......................... A61B 8/14; A61B 8/12
[52] U.S. Cl. .................. 128/662.03; 128/662.06
[58] Field of Search ............. 128/4, 6, 662.03, 662.06

[56] References Cited

U.S. PATENT DOCUMENTS

| | | | |
|---|---|---|---|
| 4,245,649 | 1/1981 | Schmidt-Andersen | 128/696 |
| 4,517,976 | 5/1985 | Murakoshi et al. | 128/4 |
| 4,519,391 | 5/1985 | Murakoshi | 128/4 |
| 4,674,515 | 6/1987 | Andou et al. | 128/662.06 |
| 4,762,002 | 8/1988 | Adams | 73/625 |
| 5,095,911 | 3/1992 | Pomeranz | 128/662.06 |

FOREIGN PATENT DOCUMENTS 1-212533  8/1989  Japan .

*Primary Examiner*—Lee S. Cohen
*Assistant Examiner*—Kevin Pontius
*Attorney, Agent, or Firm*—Frishauf, Holtz, Goodman & Woodward

[57] ABSTRACT

An ultrasonic imaging and diagnosing device comprises a section to be inserted into the body cavity, an ultrasonic wave transmitting and receiving section located at the front end of the inserting section, a conductive hollow shaft arranged in the inserting section and connected to the ultrasonic wave transmitting and receiving section, a scanning device for scanning the body cavity while changing the direction of ultrasonic wave transmitted from the ultrasonic wave transmitting and receiving section, a circuit for receiving electric signals applied from the ultrasonic wave transmitting and receiving section, and a signal cable passed through the hollow shaft to connect the ultrasonic wave transmitting and receiving section to the signal receiving circuit. Both of an outer conductive line of the signal cable and the hollow shaft are connected to the common of the signal receiving circuit to prevent noises from entering into the signal cable.

21 Claims, 18 Drawing Sheets

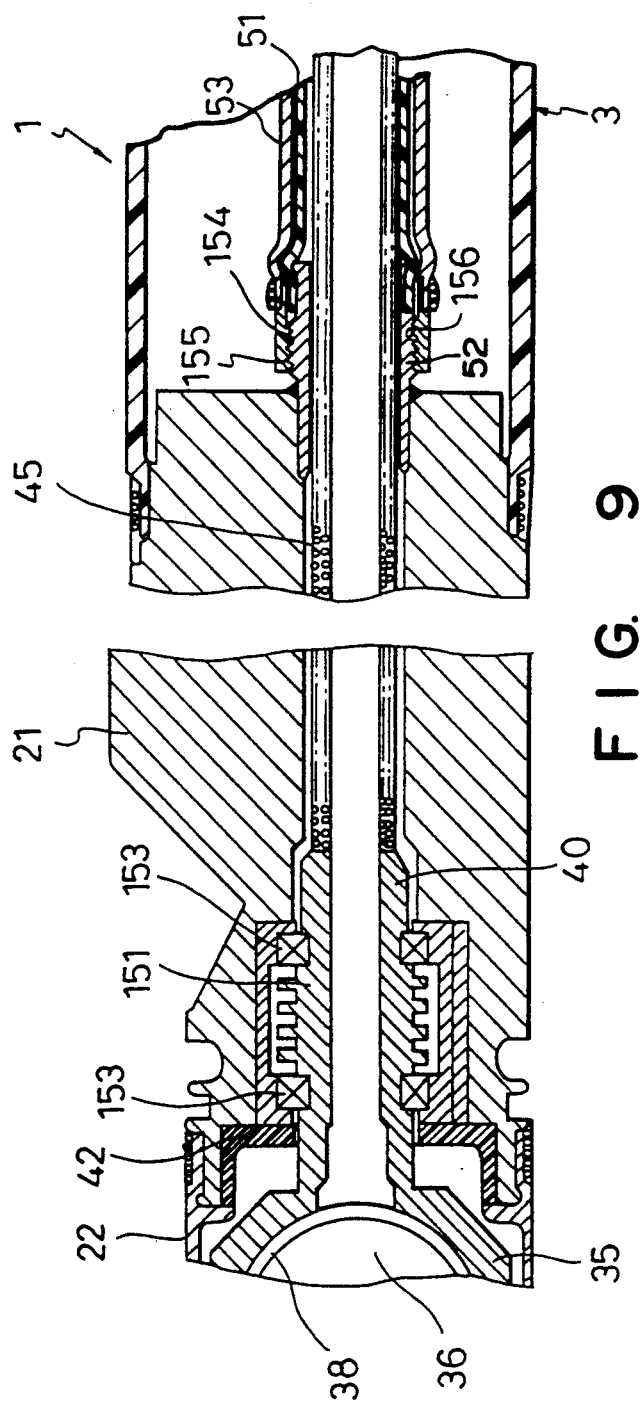

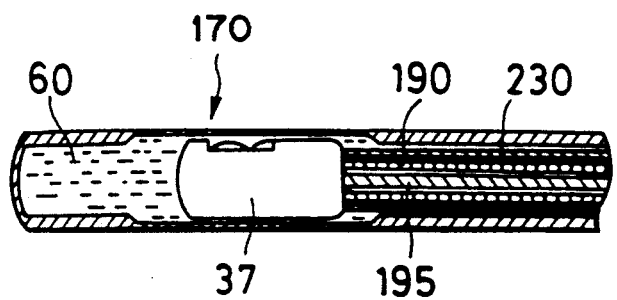
F I G. 19
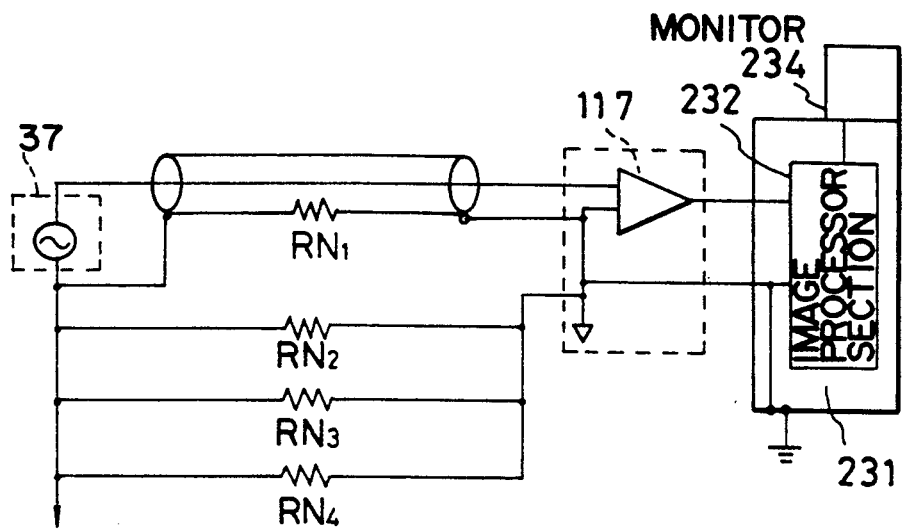
F I G. 20A
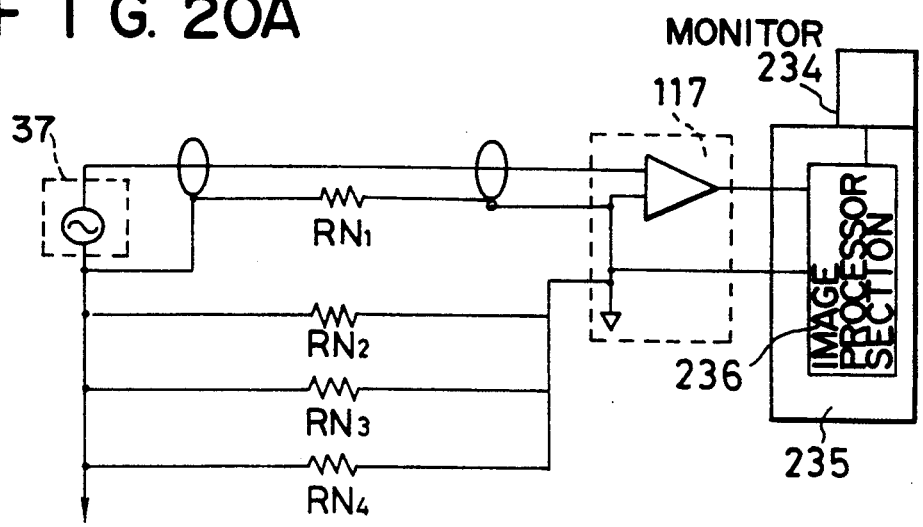
F I G. 20B

ULTRASONIC IMAGING DEVICE WITH NOISE PREVENTING STRUCTURE

BACKGROUND OF THE INVENTION

1. Field of the Invention

The present invention relates to a device for ultrasonically imaging and diagnosing the peripheral part of a cavity of a human body, said device having an ultrasonic wave transmitting and receiving section and being inserted into the body cavity to form ultrasonic sectional images of organs in the body cavity.

2. Description of the Related Art

The conventional ultrasonic image devices are well known as those having an endoscope into which the ultrasonic wave transmitting and receiving section is incorporated. The ultrasonic image devices of this kind are generally grouped into the ones of the electronic scan type and the others of the mechanical type, depending upon the manner of scanning the body cavity with ultrasonic beam applied from the ultrasonic wave transmitting and receiving section. In the case of the device of the mechanical scan type, the rotating force of the drive means such as the motor located at the endoscope operating section is transmitted to the ultrasonic wave transmitting and receiving section in the front end of the inserting section through a flexible drive shaft (or coil shaft) in the inserting section of the endoscope, so that the ultrasonic wave transmitting and receiving section can be rotatingly driven. Further, a signal received by the ultrasonic wave transmitting and receiving section is transmitted to a signal receiving circuit at the endoscope operating section through a signal cable passed through the flexible drive shaft in the inserting section.

An ultrasonic signal received by the ultrasonic wave transmitting and receiving section is quite faint and it is easily affected by noises caused by the light source for the endoscope and by the video camera located outside.

In order to solve this problem, the outer or external conductive line of the signal cable which is of the coaxial type i made low in electric resistance and it is also arranged that a single line is used in the signal cable and that the flexible drive shaft which is made by a metal coil and through which this signal cable is passed serves as the outer conductive line.

However, the signal cable and the coil shaft in the ultrasonic image device must be small in diameter, flexible, and good in curving durability. Therefore, the diameter of the outer conductive line and its material must be limited in the case of the signal cable and its diameter and material (stainless steel) must also be limited in the case of the coil shaft. This cause both of them to have high values in electric resistance. In addition, the inserting section through which both of them are passed is long, and they must be made extremely long according to the length of the inserting section. This also causes the outer conductive line of the signal cable and the coil shaft to become high in electric resistance, thereby making it unsatisfactory to shield noises outside.

In the case of the device of the electronic scan type, a solid pickup element and the ultrasonic wave transmitting and receiving section become sources for causing noises and they interact with each other to add undersirable influence to each other. When an electric process means such as the high frequency processor is used together with them, therefore, they are likely to be undesirably influenced by noises outside.

SUMMARY OF THE INVENTION

The object of the present invention is therefore to provide an ultrasonic imaging and diagnosing device capable of preventing noises from entering into the signal cable through which image signals are transmitted to form excellent ultrasonic images.

This and other objects of the present invention can be achieved by an ultrasonic imaging and diagnosing device comprising a section to be inserted into the body cavity, an ultrasonic wave transmitting and receiving section arranged in the front end of the inserting section, a conductive hollow shaft arranged in the inserting section and connected to the ultrasonic wave transmitting and receiving section, means for scanning the body cavity while changing the direction of ultrasonic wave transmitted from the ultrasonic wave transmitting and receiving section, a circuit for receiving electric signals applied from the ultrasonic wave transmitting and receiving section, a signal cable passed and guided through the hollow shaft to connect the ultrasonic wave transmitting and receiving section to the signal receiving circuit, first means including an outer conductive line of the signal cable connected to the common of the signal receiving circuit to prevent noises from entering into the signal cable, and second means including the hollow shaft connected to the signal receiving circuit to prevent noises from entering into the signal cable.

According to the device of the present invention, plural conductive lines are formed to electrically connect the common of the ultrasonic wave transmitting and receiving section to that of the signal receiving circuit, so that common impedance between the ultrasonic wave transmitting and receiving section and the signal receiving circuit can be reduced to a greater extent to prevent the entering of noises outside.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 5 is a sectional view taken along a line A—A in FIG. 3;

FIG. 9 is a horizontally-sectioned view showing the inserting section and its vicinity of the device for ultrasonically imaging and diagnosing a human body, which is realized as a third embodiment of the present invention;

FIG. 10 is a side view showing a conductive section in FIG. 9;

FIG. 19 is a sectional view showing the ultrasonic signals transmitting and receiving section of the device, which is realized as an eighth embodiment of the present invention;

FIG. 20A is an electrical block diagram showing the conductive means of the device according to the eighth embodiment of the present invention;

FIG. 20B is an electrical block diagram showing a variation of the device according to the first embodiment of the present invention.

DETAILED DESCRIPTION OF THE PREFERRED EMBODIMENTS

Some embodiments of the present invention will be described with reference to the accompanying drawings.

Figure 6:
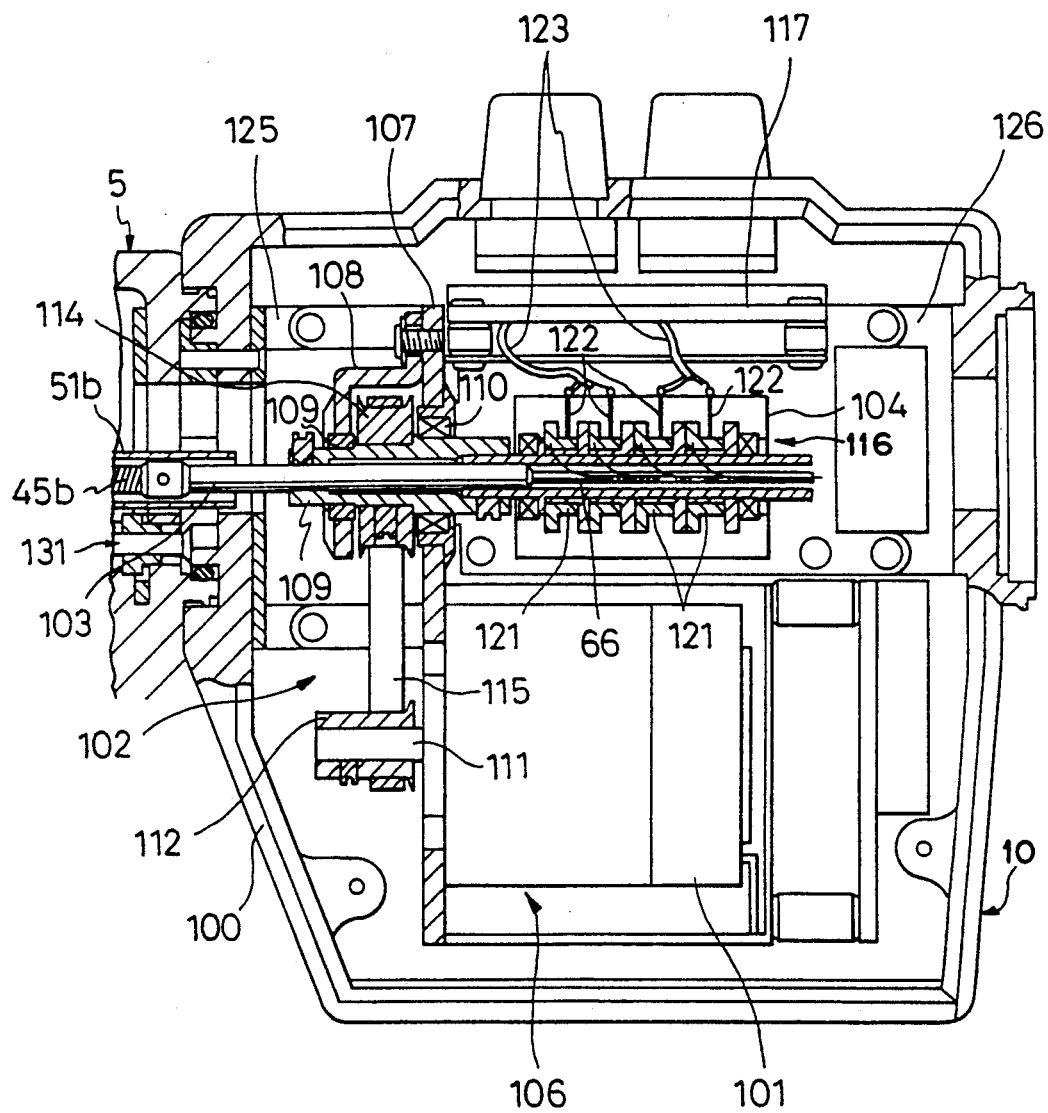
FIG. 6 is a vertically-sectioned view showing an operating subsection of the device according to the first embodiment of the present invention.
Figure 7:
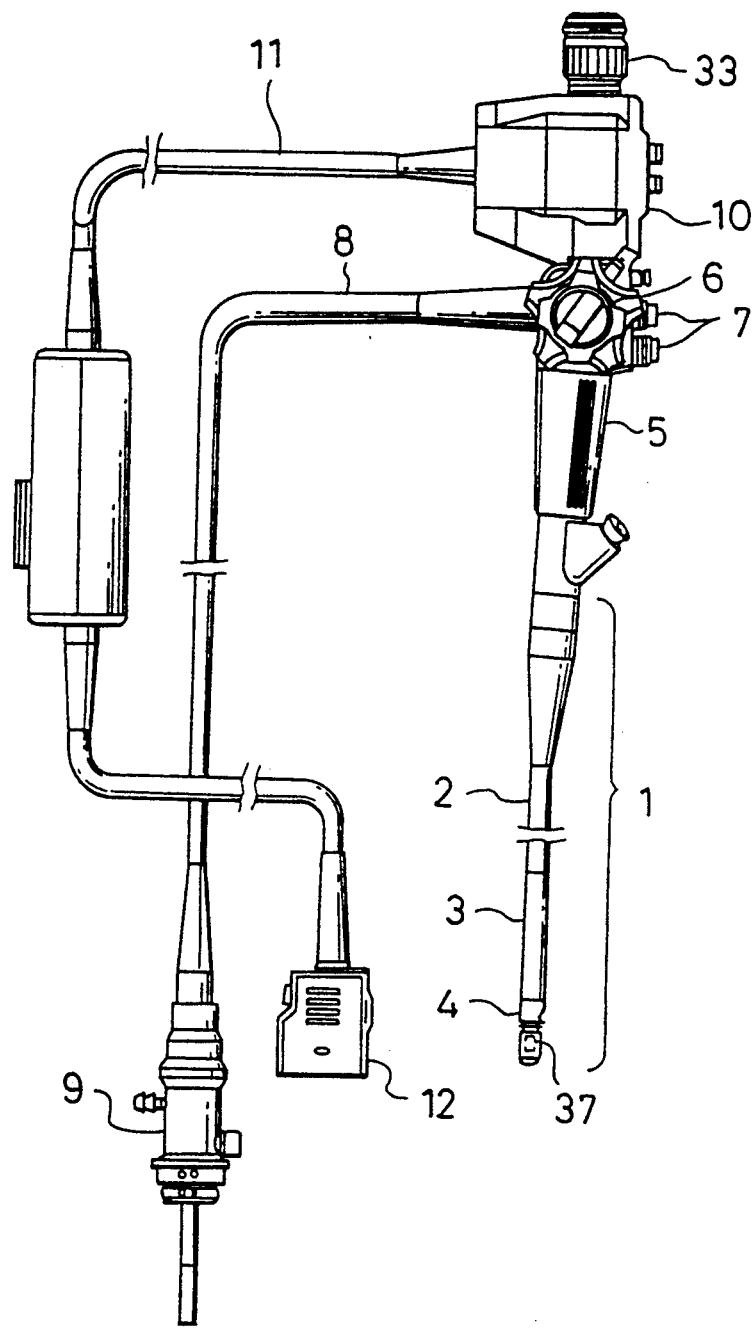
FIG. 7 shows the whole of the device according to the first embodiment of the present invention.

FIGS. 1 through 7 show a first embodiment of the present invention. FIG. 7 shows the whole of the device for ultrasonically diagnosing or imaging the cavity of a human body, which is realized as a first embodiment of the present invention, arranging an ultrasonic wave transmitting and receiving section in an endoscope. In FIG. 7, reference numeral 1 denotes an inserting section comprising a flexible tube 2, a curving tube 3 and a front end 4 connected to the front end of the flexible tube 2 via the curving tube 3. An endoscope operating section 5 is connected to the rear end of the inserting section 1. An operation knob 6 for remotely causing the curving tube 3 to be curved and buttons 7 including those for allowing air and water to be supplied are arranged at the endoscope operating section 5. A universal cord 8 is connected to the endoscope operating section 5. A connector 9 connected to a lighting light source means (not shown) is arranged at the front end of the universal cord 8. An operating subsection 10 for driving an ultrasonic vibrator is fixedly attached to the endoscope operating section 5. An electric cable 11 is connected to the operating subsection 10 at the rear end thereof and to a connector 12 at the front end thereof, while said connector 12 is connected to an ultrasonic view means (not shown).

Figure 1:
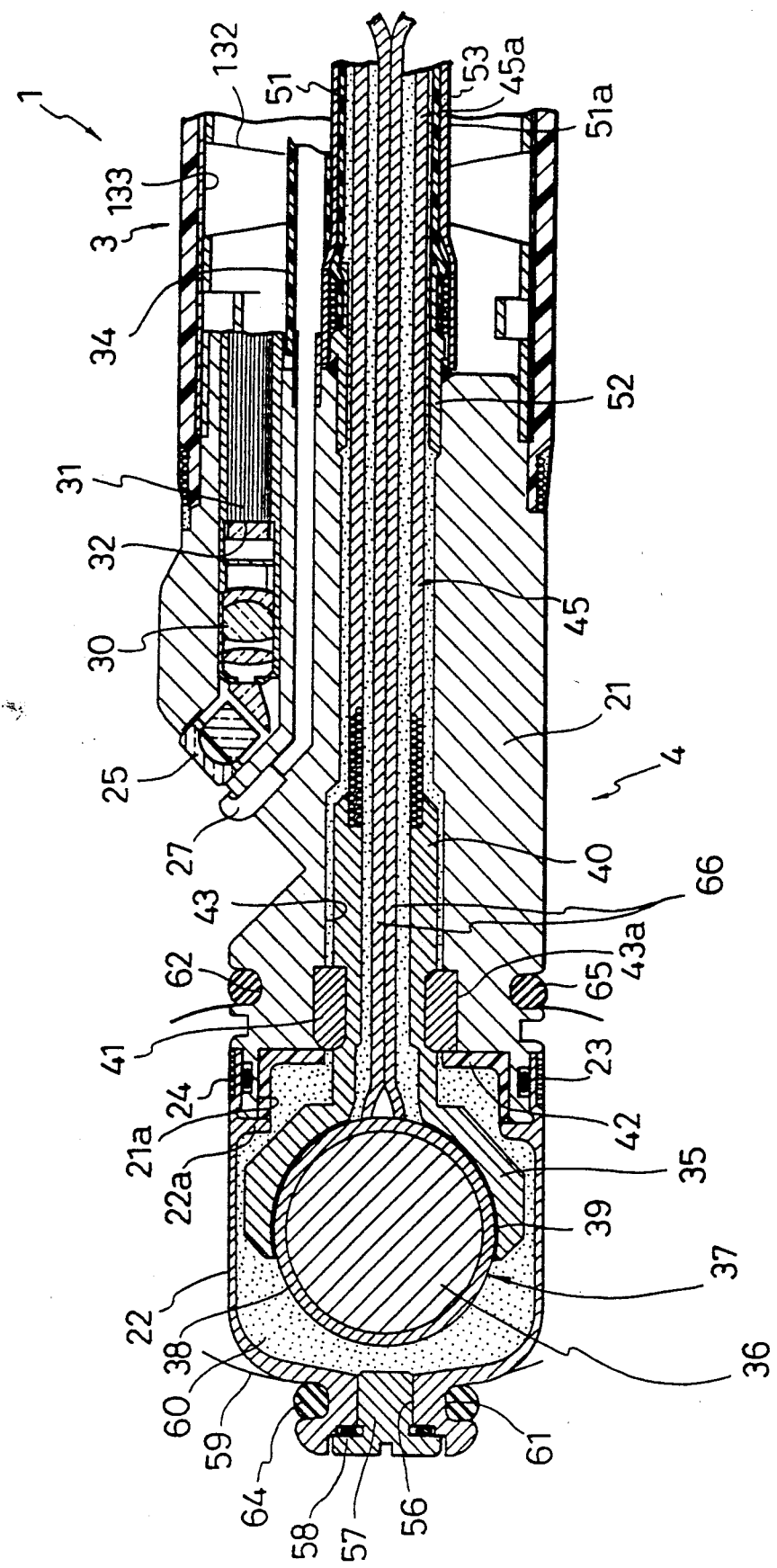
FIG. 1 is a vertically-sectioned view of an inserting section and its vicinity of the device for ultrasonically imaging and diagnosing a human body, which is realized as a first embodiment of the present invention.
Figure 2:
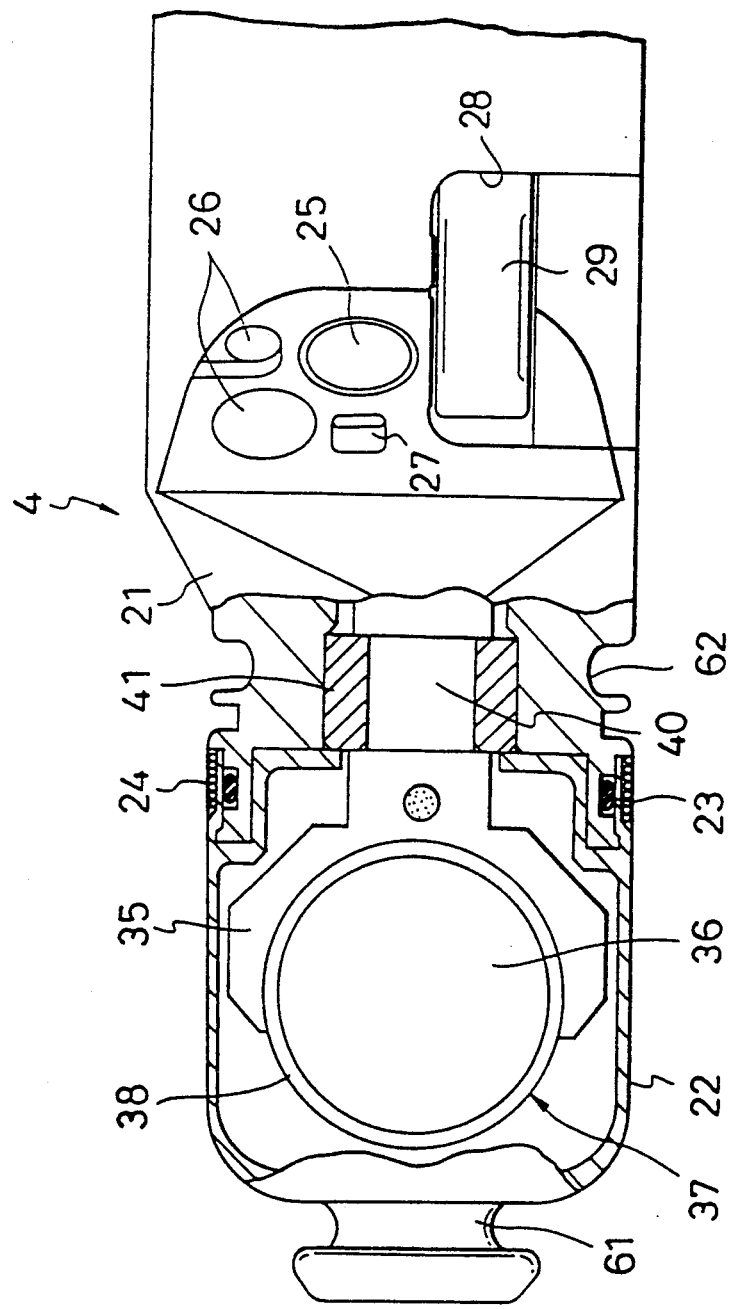
FIG. 2 is a horizontally-sectioned view showing the inserting section and its vicinity of the device according to the first embodiment of the present invention.

The front end 4 of the inserting section 1 is constructed as shown in FIGS. 1 and 2. The front end 4 includes a front end body 21 made of hard conductive material such as metal, and a front end cover 22 shaped like a ball and made of material such as polyethylene which has excellent ultrasonic wave permeability is water-tightly attached to the front of the front end body 21. The base end of the front end cover 22 is water-tightly fitted onto the front end of the front end body 21 through a sealing O-ring 23. Further, a string 24 is wound round the base end of the front end cover 22 and bonded there to increase the water-tightness of the front end cover 22 relative to the front end body 21.

As shown in FIG. 2, a viewing window 25 belonging to a viewing optical system, an illuminating window 26 belonging to an illuminating optical system, an air and water supply nozzle 27, a forceps opening 28 communicated with a forceps channel and a forceps stand 29 for the forceps opening 28 are arranged at a face of the upper portion of the front end body 21. Further, an incident front end face 32 of image guide fibers 31 is located at the focusing position of the viewing optical system 30, as shown in FIG. 1. Images focused on the incident front end face 32 are guided to an eye-piece section 33 at the operating subsection 10 through the image guide fibers 31, so that these images can be viewed by eye through the eyepiece section 33. A tube 34 which supplies air and water selectively is connected to the air and water supply nozzle 27.

An ultrasonic wave transmitting and receiving section 37 comprising a conductive probe holder 35 and an ultrasonic vibrator 36 held by the conductive probe holder 35 to transmit and receive ultrasonic waves is housed in the front end cover 22. A conductive housing 38 in which the ultrasonic vibrator 36 is housed is attached to the conductive probe holder 35 with conductive adhesive 39, for example, interposed between them. Therefore, both of the housing 38 and the probe holder 35 are electrically connected to each other. Further, one of electrodes of the ultrasonic vibrator 36 is connected to the housing 38. In short, the housing 38 is a conductive means for electrically connecting the electrode of the ultrasonic vibrator 36 to the probe holder 35. Furthermore, the probe holder 35 is electrically connected to a signals receiving circuit 117 through conductive means which will be described later, and it has the same potential as each of these conductive means.

An ultrasonic wave transmitting medium 60 such as drifting paraffin and castor oil is densely sealed in the front end cover 22. A shaft 40 of the probe holder 35 by which the ultrasonic wave transmitting and receiving section 37 is held is freely rotatably supported by a sliding bearing 41 made of conductive material. The ultrasonic wave transmitting and receiving section 3 is thus made freely rotatable in the front end cover 22. A ring-shaped spacer member 42 is fitted between a flange 22a projected from the inner face of the front end cover 22 at the rear end thereof and the bottom of a circumferential groove 21a formed on the inner face of the front end body 21 at the front end thereof. The sliding bearing 41 is fitted in a large-diameter portion 43a which is formed adjacent to the front end of the front end body 21 and on the inner circumferential face of a through-hole 43 in the front end body 21, and the spacer member 42 presses the sliding bearing 41 between the flange 22a of the front end cover 22 and the groove 21a of the front end body 21 so that the sliding bearing 41 remains in position. The spacer member 42 has holes (not shown), into which fixing pins (not shown) planted on the front end body 21 are fitted.

The sliding bearing 41 is conductive and it therefore serves as a conductive means for electrically connecting the probe holder 35 to the front end body 21. Further, the probe holder 35 is electrically connected to a conductive drive shaft 45.

The base of the probe holder 35 is connected to the front end of a flexible hollow drive shaft (or coil shaft) 45 rotated by drive means such as motors arranged at the operating subsection 10 which will be described later. The drive shaft 45 is shaped like a cylinder by two layers of closely wound coils, as shown in FIG. 1, and it is divided into a front end portion 45a and a base end portion 45b. The front end of the front end portion 45a is fixedly embedded in the base of the shaft 40 which is the cylindrical base of the probe holder 35.

A water-tight flexible guide tube 51 is communicated with the through-hole 43 in the front end body 21 via a connecting pipe 52 made of conductive material. The guide tube 51 is made of urethane, for example, and divided into a front end portion 51a and a rear end portion 51b. The outer circumference of the front end portion 51a of the guide tube 51 is covered by a cylindrical shield member 53, which is shaped like a cylindrical pipe by winding a material of good conductivity such as a wire of brass and soldering front and rear ends of the brass wire thus wound. The front end of the shield member 53 is electrically connected to the conductive front end body 21 via the connecting pipe 52, while the rear end thereof is also electrically connected a base plate 90 of the endoscope operating section 5 through conductive means which will be described later.

The drive shaft 45 is guided rearward, passing through a passage which is formed by the through-hole 43 and the guide tube 51 connected to the rear end of the through-hole 43 via the connecting pipe 52. The ultrasonic wave transmitting medium 60 is densely filled between the drive shaft 45 and the inner faces of the through-hole 43 and the guide tube 51 through which the drive shaft 45 passes.

An opening 56 through which the ultrasonic wave transmitting medium is injected into the front end cover 22 is formed at the front end wall of the cover 22 in the center thereof and it is sealed by screwing a sealing screw 57 into it through an O-ring 58. Grooves are formed on front and rear outer circumferences of the front end cover 22, respectively, and balloon stoppers 61 and 62 for stopping front and rear rims of a balloon 59 (only a part of which is shown) are arranged in the grooves. The front and rear rims of the balloon 59 are seated in the stopper grooves 61 and 62 and fastened and water-tightly fixed there by fastening rings 64 and 65 to water-tightly cover the outer circumference of the front end cover 22 by the balloon 59. Passages for supplying and discharging water into and from the balloon 59 are arranged in the inserting section 1.

Two signal cables 66 connected to the ultrasonic wave transmitting and receiving section 37 pass through the drive shaft 45. Each of the signal cables 66 is of coaxial type and it extends from the rear end of the inserting section 1 to the connector 12, passing through the endoscope operating section 5, the operating subsection 10 and the electric cable 11, and it is then connected to a transmitting and receiving circuit of the ultrasonic view means (not shown).

Figure 3:
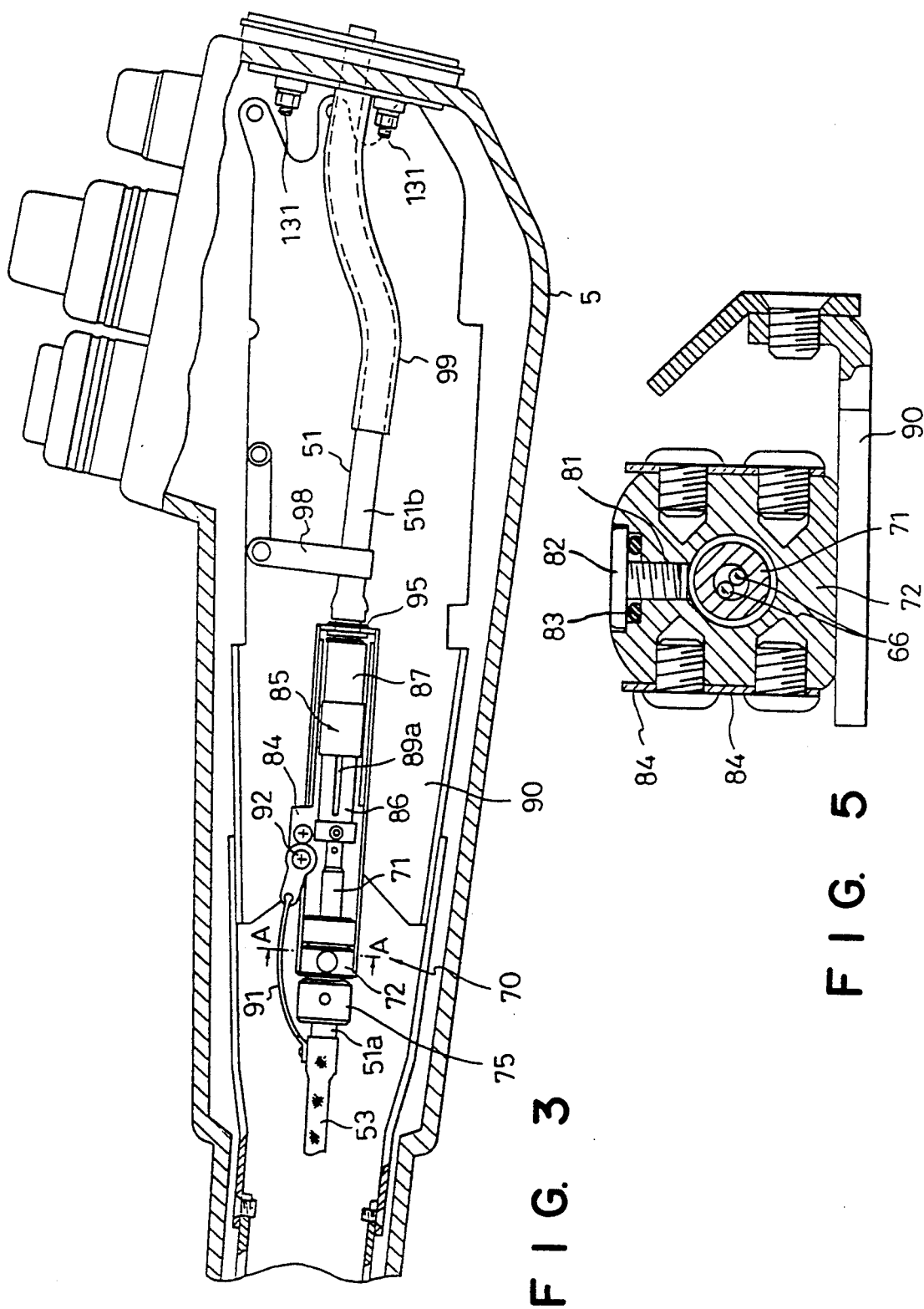
FIG. 3 is a vertically-sectioned view showing an endoscope operating section of the device according to the first embodiment of the present invention.
Figure 4:
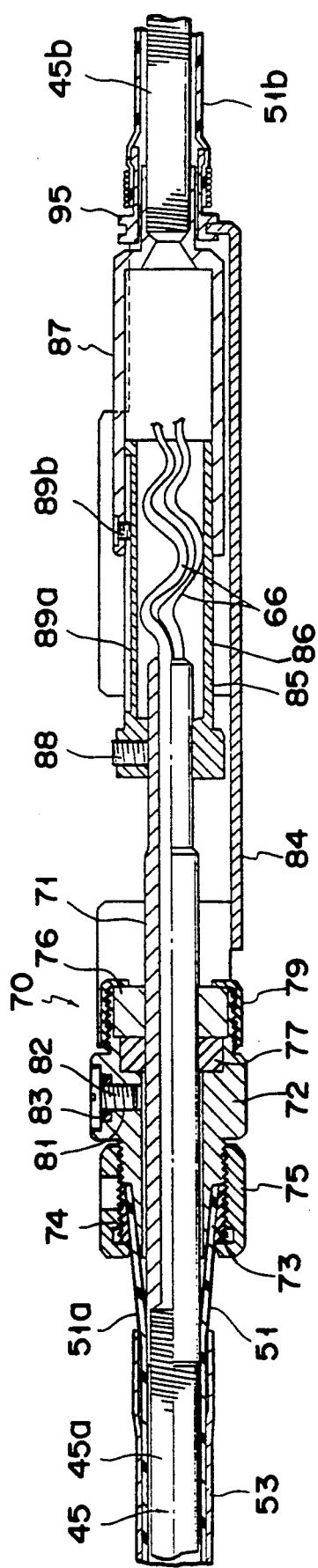
FIG. 4 is a vertically-sectioned view showing a sealed section of the device according to the first embodiment of the present invention.

On the other hand, a shaft seal section 70 which has such an arrangement as shown in FIGS. 3 through 5 is attached to the drive shaft 45 and the guide tube 51 on the way thereof in the endoscope operating section 5. More specifically, a hollow seal shaft 71 in which the signal cables 66 are water-tightly sealed is connected to the rear end of the front end portion 45a of the drive shaft 45 and a cylindrical seal holder 72 is fitted onto the shaft 71. The rear end rim of the front end portion 51a of the guide tube 51 is fitted onto a tapered outer circumference 73 of the front end of the seal holder 72 and water-tightly pressed by a press ring 74 which has an inner circumference tapered to match the tapered outer circumference 73 of the seal holder 72. Arranged in the rear end of the seal holder 72 are a bearing 76 for freely rotatably holding the shaft 71 and a seal member 77 capable of water-tightly sliding on the outer circumference of the shaft 71. A fixing ring 79 is screwed onto the rear end of the seal holder 72 to press the bearing 76 and the seal member 77 against the shaft 71. The inside of the front end portion 51a of the guide tube 51 is thus water-tightly sealed. The bearing 76 is made of conductive material and, using this bearing as a conductive means, the conductive shaft 71 connects the drive shaft 45 electrically to a support frame 84, which will be described later, via the conductive seal holder 72.

Further, a through-hole 81 communicated with the front end portion 51a of the guide tube 51 is formed in the wall of the seal holder 72 and it is sealed by screwing a sealing screw 82 into it through an O-ring 83. The ultrasonic wave transmitting medium 60 sealed in the front end portion 51a of the guide tube 51 can be prevented from leaking out of it.

The seal holder 72 is held by the support frame 84. Further, the rear end of the sealing shaft 71 is connected to a connecting sleeve 85 which is freely rotatable relative to the support frame 84. The connecting sleeve 85 comprises a front portion 86 and a rear portion 87 and the shaft 71 is fitted into the front portion 86 of the sleeve 85 and fixed there by a set screw 88 which is screwed into the front portion 86. The rear end of the front portion 86 is freely slidably fitted into the rear portion 87. A guide groove 89a is formed on the outer circumference of the front portion 86 along the axial direction of the connecting sleeve 85 while the rear portion 87 is provided with a pin 89b which is engaged with the guide groove 89a on the front portion 86. Both of the front and rear portions 86 and 87, therefore, can not rotate but slide relative to each other in the axial direction thereof. When arranged in this manner, the connecting sleeve 85 can be made telescopic in the axial direction thereof. The support frame 84 at the shaft seal section 70 is fixed to the conductive base plate 90 in a casing located on the side of the endoscope operating section 5.

A conductive cable 91 whose one end is connected to the rear end of the shield member 53 is attached to the support frame 84 of the shaft seal section 70 at the other end thereof by a screw 92. When the cable 91 is to be attached in this manner by the screw 92, both of the support frame 84 and the base plate 90 are fixed at the same time and the support frame 84 serves as a conductive means for electrically connecting the cable 91 to the base plate 90. Therefore, the shield member 53 is electrically connected to the common of the signals receiving circuit 117 through tractive members 125 and 126 at the operating subsection 10, as will be described later, and it has the same potential as the common of the circuit 117. The rear end portion 51b of the guide tube 51 is supported by the base plate 90 through a metal holder 98 and covered by a protection tube 99.

The front end of the base end portion 45b of the drive shaft 45 is connected to the rear portion of the connecting sleeve 85. The rear end portion 45b is passed through the rear end portion 51b of the guide tube 51. The front end of the rear end portion 51b of the guide tube 51 is attached to the support frame 84 by a metal fitting 95.

The operating subsection 10 is arranged as shown in FIG. 6. A motor 101 which serves as a drive source is housed in a case 100. The rotation of the motor 101 is transmitted to an output shaft 103 through a declaration system 102. The output shaft 103 is set coaxial to the inserting section 1. A rotation detector section 104 is located at one end of the output shaft 103, while the other end of the output shaft 103 is connected to the rear end portion 45b of the flexible drive shaft 45 which is inserted into the inserting section 1.

The base end of the rear end portion 51b of the guide tube 51 is introduced into the conductive case 100 at the operating subsection 10 and the output shaft 103 is connected to the base end of the rear end portion 45b of the drive shaft 45 which is guided by the guide tube 51.

Further, a drive unit 106 into which the motor 101 is incorporated is housed in the case 100. The drive unit 106 comprises a base 107, a shaft holder 108 arranged on the base 107, and a hollow output shaft 103 freely rotatably supported through a bearing 109 held by the shaft holder 108 and through another bearing 110 held by the base 107. A pulley 112 is attached to the drive shaft 111 of the motor 101 and another pulley 11 is attached to the output shaft 103. A belt 115 is stretched between the pulleys 112 and 114 to form the declaration system 102.

The signal cables 66 which are connected to the ultrasonic probe 37 are passed through the hollow output shaft 103. The signal cables 66 are connected to the signals receiving circuit 117 via a signals transmitting section 116 of the rotation type which is connected to the rear end of the output shaft 103. The signals transmitting section 116 of the rotation type comprises slip rings 121 which rotate together with the output shaft 103, and brushes 122 which are contacted with the slip rings 121 First ends of the signal cables 66 are connected to the slip rings 121 and first ends of signal cables 123 which are connected to the signals receiving circuit 117 are connected to the brushes 122. Formed on those faces of the adjacent slip rings 121 which are opposed to each other are layers of ceramic coat to prevent these adjacent slip rings 121 from being electrically connected to each other. Signals received from the ultrasonic waves transmitting and receiving section 37 are transmitted to the signals receiving circuit 117 via the signals transmitting section 116 and amplified there.

The base 107 in the case 100 is held by the case 100 through the tractive members 125 and 126 located at the front and rear of the case 100. The base 107 is electrically connected to the tractive members 125 and 126 by a conductive means, which is formed by fixing members and lead lines, in such a way that the potential of the tractive members 125 and 126 becomes equal to the common potential of the signals receiving circuit 117. The shield line of a control cable (not shown) for the motor 101 is also electrically connected to the tractive members 125 and 125 to have the same potential as these tractive members 125 and 126. The shield line of the motor cable (not shown) is electrically connected to the common of the signals receiving circuit 117 by the conductive case 100.

Further, the tractive members 125 and 126 are electrically connected to the casing located on the side of the endoscope operating section 5 or to the conductive base plate 90 in the casing through fixing screw 131, which serve to connect the operating subsection 10 to the endoscope operating section 5, and the like and they have the same potential as the casing or base plate 90.

As shown in FIG. 1, the curving pipe 3 at the inserting section 1 comprises a coating on the outer circumference of a core, which consists of a plurality of curving tops 132 freely rotatably connected to one another, with a conductive braid 133 made of metal. The front end of the conductive braid 13 is electrically connected to the conductive front end body 21 and it serves as a third conductive means. The braid 133 is connected to the common potential of the signals receiving circuit 117 through a conductive braid (not shown) of the flexible pipe 2 at the inserting section 1 and also through the case 100 and the base plate 90 at the endoscope operating section 5 and the tractive members 125 and 126 at the operating subsection 10. The braid 133 thus has the same potential as the common of the signals receiving circuit 117. In short, the braid 133 at the inserting section 1 is electrically connected to the front end body 21 to achieve shield effect.

According to the first embodiment of the present invention having the above-described arrangement, those lines through which the ultrasonic vibrator 36 is electrically connected to the signals receiving circuit 117 can be totaled to four including the one formed only through the external conductive line of the signal cables 66 and the other three formed through the drive shaft 45, through the shield member 53 and through the braid 133 which is a component of the inserting section 1, the other three lines being established by interposing the conductive slide bearing 41 between the shaft 40 of the conductive probe holder 35 and the conductive front end body 21. These lines serve to shield the signal cables 66 and the composed impedance of them is lower than the impedance of each of them, so that impedance common to the ultrasonic wave transmitting and receiving section 37 and the signal cables 66 can be lowered.

Further, the three conductive lines are formed using the slide bearing 41 which serves to support the probe holder 35. As compared with the ball bearing, therefore, the slide bearing 41 can serve as a bearing and as a conductive means, thereby enabling the front end section 4 to be made simpler in construction and to be prevented from becoming larger in size. The patient can thus feel less pain when the inserting section 1 of the device is inserted into his body cavity. In addition, the slide bearing 41 is higher in conductivity than the ball bearing.

FIG. 20A is a block diagram showing the conductive lines in the first embodiment of the present invention. When the conductive lines extending from the ultrasonic wave transmitting and receiving section 37 to the common of the signals receiving circuit 117 are made plural as shown in FIG. 20A, the total resistance R of them becomes lower than resistance $RN_1$ of only the external conductive line of the signal cables 66. The impedance of the conductive lines becomes lower accordingly, so that noises can be prevented more effectively. Providing that $RN_2 = 2RN_1$, $RN_3 = \frac{1}{2}RN_1$ and $RN_4 = RN_1$, the total resistance R can be calculated as follows:

$$
\begin{aligned}
1/R &= 1/RN_1 + 1/RN_2 + 1/RN_3 + 1/RN_4 \\
&= 1/RN_1 + 1/2RN_1 + 2/RN_1 + 1/RN_1 \\
&= 9/2RN_1 \\
R &= 2/9RN_1
\end{aligned}
$$

Therefore, the total resistance R is 2/9 of resistance $RN_1$.

Needless to say, the same shield effect can be attained relative to noises outside when the signals receiving circuit 117 is connected to an images processing section 232 of a view means 231 whose secondary electronic circuit is earthed, as shown in FIG. 20A and when it is connected to an images processing section 236 of a view means 235 whose secondary electronic circuit is not earthed, as shown in FIG. 20B.

Figure 21:
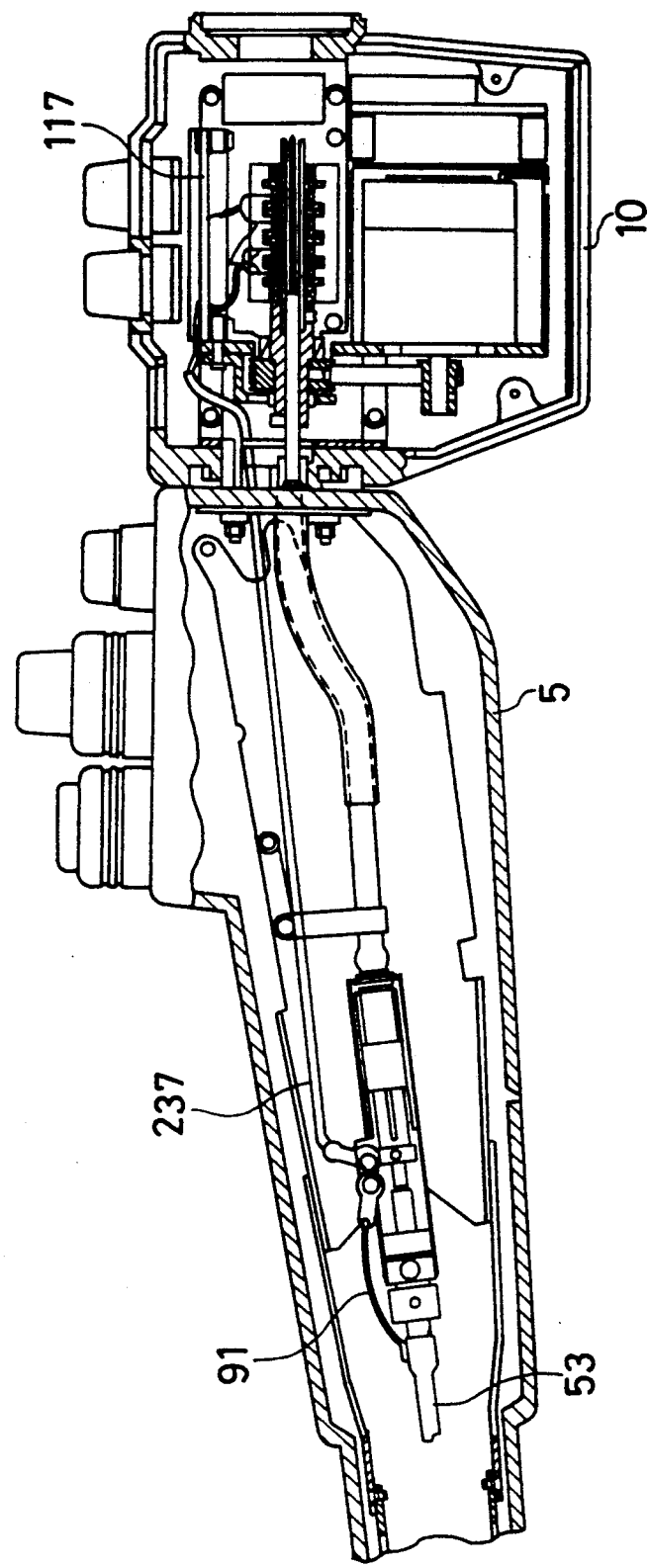
FIG. 21 is a partly-sectioned view showing another variation of the device according to the first embodiment of the present invention.

Although the shield member 53 and the signals receiving circuit 117 have been electrically connected to each other, using the base plate 90 and the tractive members 125, 126, in the case of the first embodiment of the present invention, they may be connected to each other by a cable 237, as shown in FIG. 21.

Figure 8:
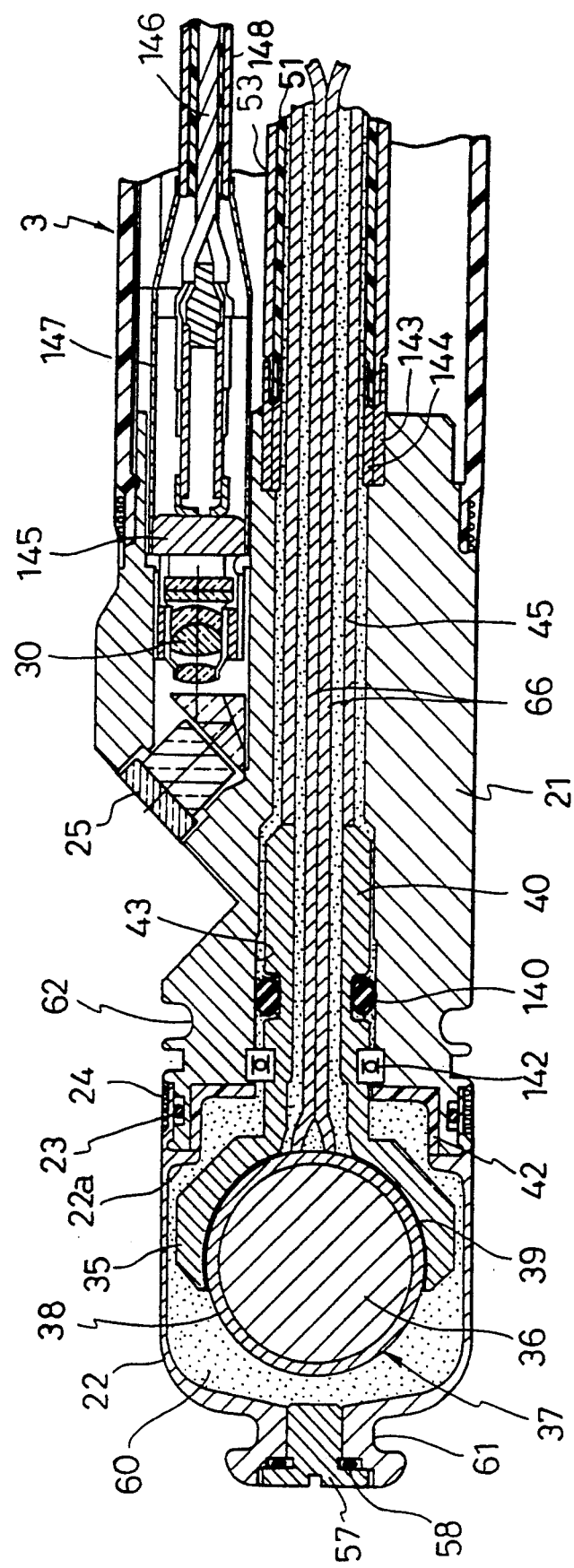
FIG. 8 is a horizontally-sectioned view showing the inserting section and its vicinity of the device for ultrasonically imaging and diagnosing a human body, which is realized as a second embodiment of the present invention.

FIG. 8 shows a second embodiment of the present invention. A ball bearing 142 is used instead of the slide bearing 41 in this case to support the shaft 40 of the probe holder 35 which holds the ultrasonic vibrator 36. Further, a conductive elastic O-ring 140 is interposed between the shaft 40 of the probe holder 35 and the front end body 21. The shaft 40 of the probe holder 35 and the front end body 21 are thus electrically connected to each other mainly through the elastic O-ring 140.

Still further the guide tube 51 and the shield member 53 piled double are interposed between conductive pipes 143 and 144 and made integral to the pipes by swaging. These portions of the pipes which have been made integral together with the guide tube 51 and the shield member 53 are mechanically and electrically connected to the front end body 21 by soldering. When arranged in this manner, the guide tube 51, the shield member 53 and the conductive pipes 143, 144 are formed as a unit which can be made smaller in diameter and simpler in structure.

Still further, a solid pickup element 145 is located at a focusing point of the viewing optical system 30 instead of the image guide fibers 31, and a pickup signal cable 146 is connected to the solid pickup element 145. A shield means is applied to each of these solid pickup element 145 and pickup signal cable 146. More specifically, the solid pickup element 145 is covered by a shield cover 147 and the pickup signal cable 146 by a cylindrical shield member 148. These shield cover and member 147 and 148 are electrically connected to the front end body 21, the base plate 90 at the endoscope operating section 5 and the like.

FIGS. 9 and 10 show a third embodiment of the present invention. A slip ring 151 is attached, instead of the conductive slide bearing 41, to the shaft 40 of the probe holder 35 and each bundle of brush 152 is located to slidably contact that side of each ring-shaped projection of the slip ring 151 which is directed to the side of the front end body 21, thereby forming a conductive means for electrically connecting both of the probe holder 35 and the front end body 21. Further, bearings 153 and 153 are provided, independently of this conductive means, to support the shaft 40 of the probe holder 35. Since the slip ring 151 and the brush 152 slidably contacted with the slip ring 151 are used, as described above, to electrically connect the probe holder 35 to the front end body 21, electric conductivity between them can be made more reliable, noises can be more reliably prevented and more stable ultrasonic images can be obtained.

A male screw thread 154 is formed on the outer circumference of the connecting pipe 52 and a female screw thread 156 is formed on the inner circumference of a metal-made pipe 155 which is connected to the shield member 53, so that the pipe 155 can be screwed onto the connecting pipe 52. Therefore, the shield member 53 can be more easily attached to and detached from the connecting pipe 52 to thereby make shorter the time needed for repairs and the time needed for starting the diagnosis of a waiting patient.

Figure 11:
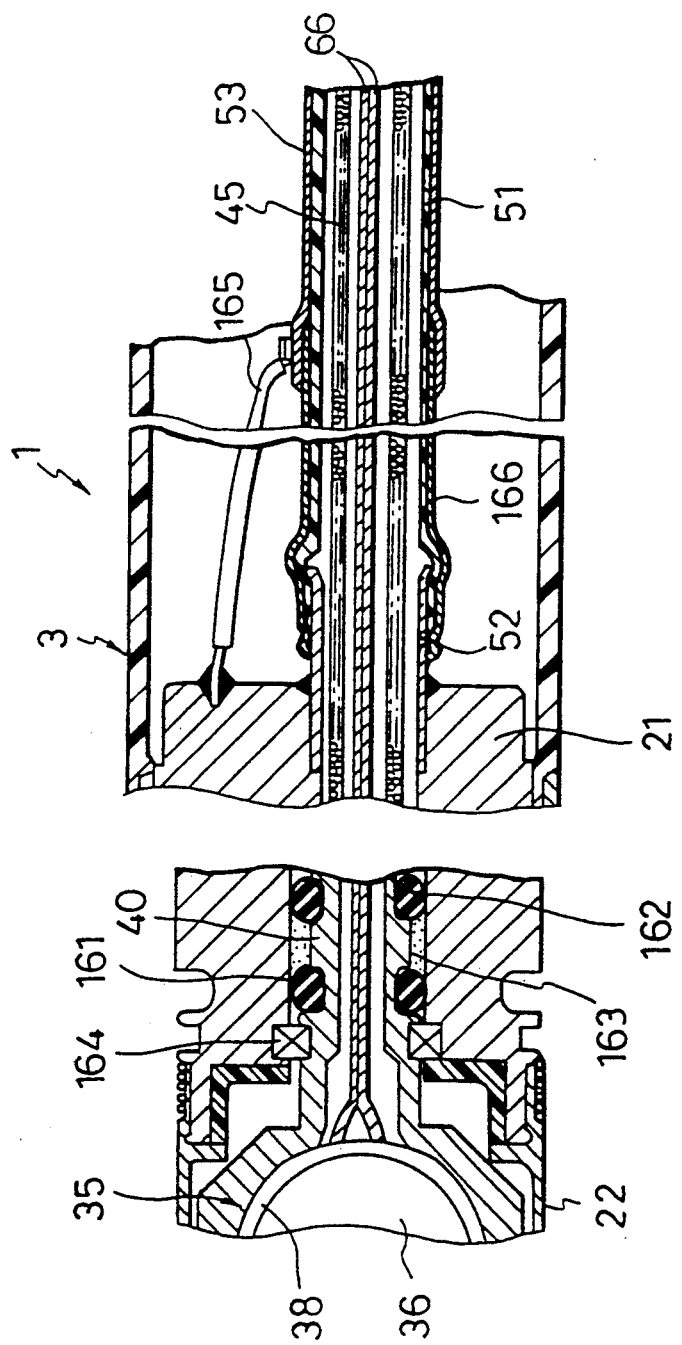
FIG. 11 is a horizontally-sectioned view showing the inserting section and its vicinity of the device for ultrasonically imaging and diagnosing a human body, which is realized as a fourth embodiment of the present invention.

FIG. 11 shows a fourth embodiment of the present invention. Two conductive elastic O-rings 161 and 162 are used instead of the elastic O-ring 40 in the second embodiment and conductive grease 163 is sealed in a space between these two elastic O-rings 161 and 162 in this case. Electric conductivity between the side of the front end body 21 and the side of the probe holder 35 can be thus further enhanced.

Further, the shaft 40 of the probe holder 35 is supported by a bearing 164.

Still further, the front end body 21 and the shield member 53, each made of conductive material, are electrically connected to each other through a conductive cable 165. Still further, the connecting pipe 52 of the front end body 21 and the shield member 53 are electrically connected to each other via a flex 166 which extends from the connecting pipe 52 to the front end of the shield member 53. This flex 166 is made conductive by making it of phosphor bronze or plating its surface with metal, and it is fitted onto the guide tube 51.

According to the fourth embodiment of the present invention having the above-described arrangement, the front end body 21 and the shield member 53 are electrically connected to each other via the conductive cable 165. Therefore, attachment and detachment of the shield member 53 at the inserting section 1 can be made easier to thereby enable the inserting section 1 to become more advantageous to repairs. The diameter of the shield member 53 can also be prevented from becoming large because it is not needed that the shield member 5 is attached to the flex 166 by adhesive or soldering. The diameter of the inserting section 1 can be thus made smaller. Further, the guide tube 51 is covered by the flex 166. This enables the bending capacity of the inserting section 1 to be further enhanced and the drive shaft 45 to be more smoothly rotated not to disturb images formed.

FIGS. 12 through 15 show a fifth embodiment of the present invention.

Figure 12:
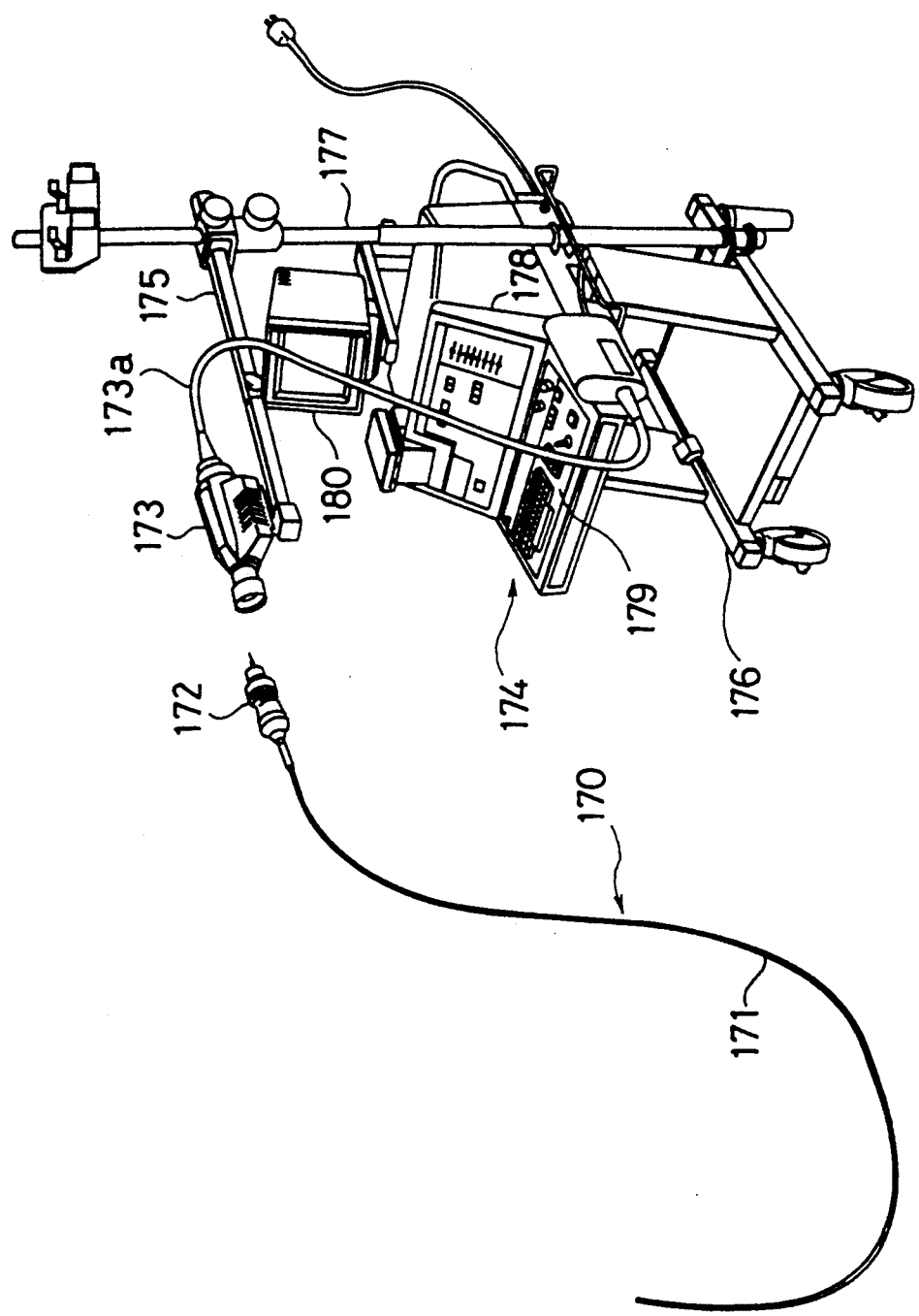
FIG. 12 is a perspective view showing the whole of the device for ultrasonically imaging and diagnosing a human body, which is realized as a fifth embodiment of the present invention.

As shown in FIG. 12, an inserting section 170 in this case has a flexible slender sheath 171 which can be inserted into the body cavity such as hepatic duct and blood vessel directly or via a channel in the endoscope and into the front end of which a probe unit having an ultrasonic probe 186 which will be described later is freely rotatably incorporated. The inserting section 170 has a connecting connector 172 at the base end thereof and it is connected to a drive operating section 173 by the connecting connector 172. The drive operating section 173 is connected to an ultrasonic view means 174 via a cord 173a. An arm 175 for supporting the drive operating section 173 is attached to a pole brace 177 erected from a carriage 176 on which the ultrasonic view means 174 is mounted. The ultrasonic view means 174 includes a body 178 into which the images processing circuit and the like are incorporated, a keyboard 179 and a TV monitor 180.

Figure 13:
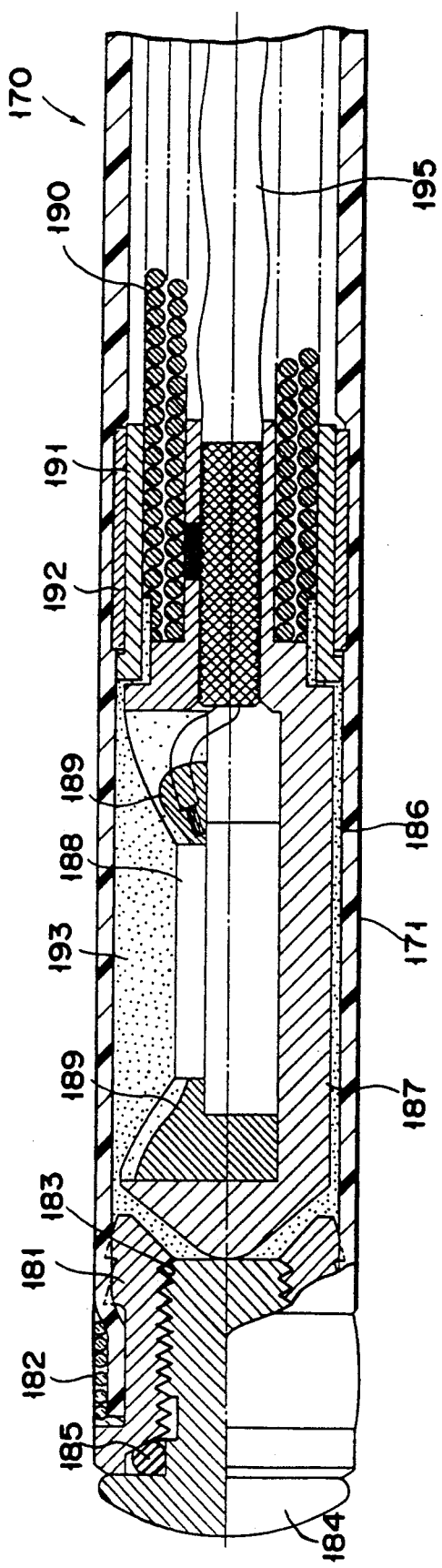
FIG. 13 is a vertically-sectioned view showing the inserting section and its vicinity of the device according to the fifth embodiment of the present invention.

The inserting section 170 is shown in more detail in FIG. 13. A cylindrical front frame 181 is fitted into the front end of the teflon-made sheath 171 and watertightly fixed there by a string 182 wound round the front end of the sheath 171. A set screw 184 is screwed into an opening 183 in the front frame 181 to seal the opening 183. A sealing O-ring 185 is interposed between the front frame 181 and the set screw 184.

An ultrasonic wave transmitting and receiving section 186 is freely rotatably arranged in the front end of the sheath 171.

The ultrasonic wave transmitting and receiving section 186 comprises attaching an ultrasonic vibrator 188 to a probe holder 187 by conductive adhesive 189. The front end of a drive shaft 190 which comprises a metal-made coil is fitted onto the rear end of the probe holder 187 and both of the drive shaft 190 and the probe holder 187 are made electrically conductive by being fixed there by adhesive and laser welding. A second conductive means is thus formed. Both of the drive shaft 190 and the probe holder 187 are connected to each other by adhesive and welding to thereby enhance their mechanical strength and electric conductivity.

A slide ring 191 is fixedly fitted onto the front end of the drive shaft 190 to which the probe holder 187 is fixed. The slide ring 191 is slidably contacted with and rotatably supported by the inner face of a seat 192 which is shaped like a short pipe and which is pressed into the front end of the sheath 171 and fixed there. An ultrasonic wave transmitting medium 193 such as liquid paraffin is densely filled in a closed space in which the probe holder 187 for holding the ultrasonic vibrator 188 is housed. A signal cable 195 connected to the ultrasonic vibrator 188 is of the coaxial type and it extends rearward, passing through the drive shaft 190. The core line of the signal cable 195 is connected to the plus side of the ultrasonic vibrator 188 by conductive adhesive 189. The common of the ultrasonic vibrator 188 is electrically connected to the external conductive line of the signal cable 195 by soldering the external conductive line of the cable 195 to the probe holder 187. A third conductive means is thus formed.

The conductive adhesive 189 is coated by watertight adhesive such as epoxy.

Figure 14:
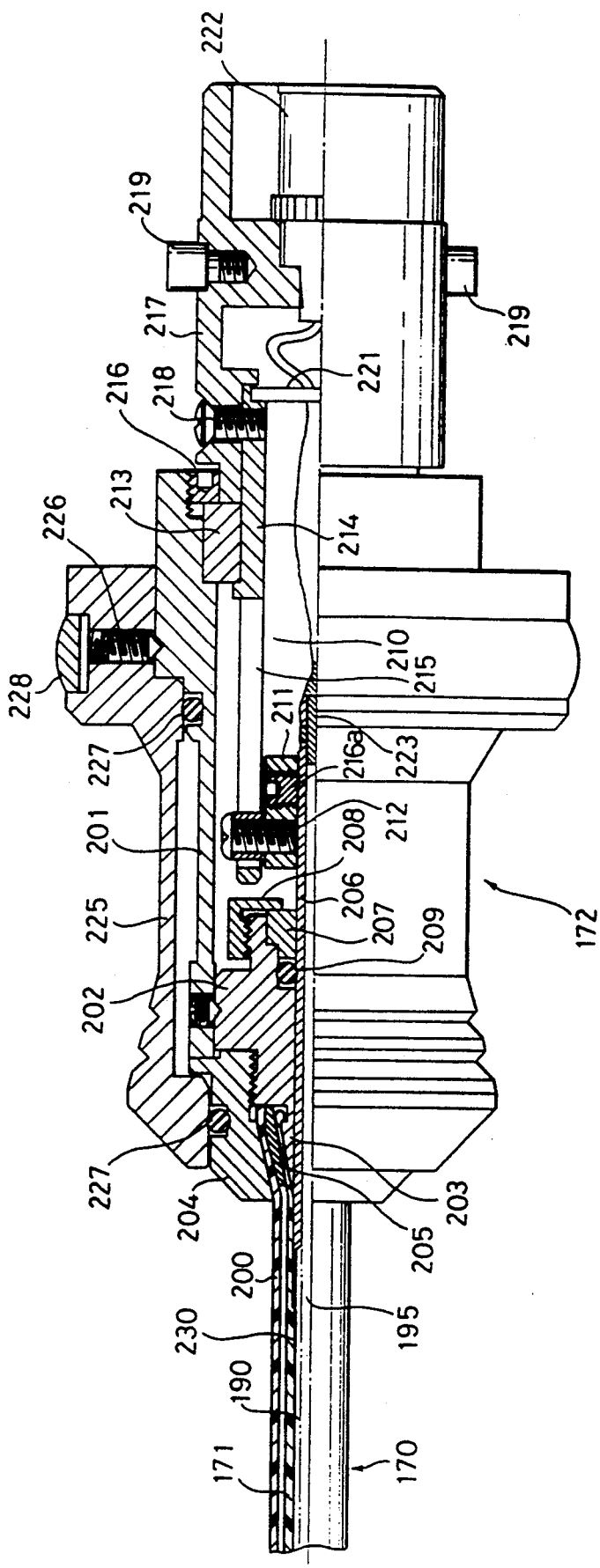
FIG. 14 is a vertically-sectioned view showing a connecting connector section of the device according to the fifth embodiment of the present invention.

The connector 172 attached to the base end of the inserting section 170 is arranged as shown in FIG. 14. The rear end of the sheath 171 is forcedly fitted onto a tapered front end 203 of a connecting body 202 which is fitted and fixed in the front end of a cylindrical connector body 201, and fastened and fixed there by a lock nut 204. A bending stopper tube 200 is fitted onto the rear end of the sheath 171. The base end of the bending stopper tube 200 is fitted into the lock nut 204, locating on the rear end of the sheath 171 with a tapered ring 205 interposed between them, and fastened and fixed together with the rear end of the sheath 171 by the lock nut 204. The rear end of a braid 230 which will be described later located inside the lock nut 205 this time is fastened and fixed by the nut 205.

The front end of a pipe-shaped metal fitting 206 is fitted into the rear end of the drive shaft 190 and fixed there by soldering. The metal fitting 206 passes through the connecting body 202 and it is freely rotatably supported by a conductive bearing 207 which is attached to the rear end of the connecting body 202. The bearing 207 is fixed to the connecting body 202 by a fixing ring 208. The drive shaft 190 is electrically connected to the connector and connecting bodies 201 and 202 directly through the metal fitting 206 or through the conductive bearing 207. An O-ring 209 is interposed between the connecting body 202 and the metal fitting 206 to establish sealing between them A slide system 210 for guiding the metal fitting 206 in the axial direction is incorporated into the connector body 201. More specifically, a slider 211 is fixedly fitted onto the base end of the metal fitting 206 and a slider pin 212 is projected from the slider 211. A slider ring 214 freely rotatably supported by a conductive bearing 213 is arranged in the connector body 201 and a slide groove 215 is formed in the slider ring 214 in the axial direction thereof. The slider pin 212 is in the slide groove 215 and the slider 211 and the metal fitting 206 are thus allowed to move relative to the slider ring 214 only in the axial direction and in a range which is equal to the length of the slide groove 215. The slider 211 and the metal fitting 206 are also rotated together with the slider ring 214 round the axial center line thereof while holding the slider pin 212 in the slider groove 215 of the slider ring 214. The metal fitting 206 and the slider 211 are fixedly connected to each other by a set screw 216a. The bearing 213 and the slider ring 214 are supported by the connector body 201 through a fastening ring 216 and a conductive connector pipe 217. The slider ring 214 and the connector pipe 217 are fixedly connected to each other by a set screw 218 and they are not moved in the axial direction but rotated like a unit. A pair of rotation receiving pins 219 are attached to the outer circumference of the connector pipe 217, projecting their heads outside from the pipe 217.

The signal cable 195 which passes through the drive shaft 190 is introduced into the connector body 20 through the metal fitting 206 and connected to a coaxial connector 222 in the connector pipe 217 via a base plate 221 which is attached to the rear end of the slider ring 214 and in which a matching coil is housed. To add more, the signal cable 195 is fixedly connected to the metal fitting 206 through conductive adhesive 223 and then to the coaxial connector 222 via the base plate 221. The coaxial connector 222 is electrically connected to components located on the side of the drive operating section 173 when the connecting connector 172 is connected to the drive operating section 173.

A cylindrical grip member 225 is fitted onto the connector body 201 and fixed by a set screw 226. Two sealing O-rings 227 are interposed between the connector body 201 and the grip member 225 at the front and rear thereof. A click O-ring 228 is freely detachably fitted onto the grip member 225 when this grip member 225 is to be connected to the drive operating section 173.

Figure 15:
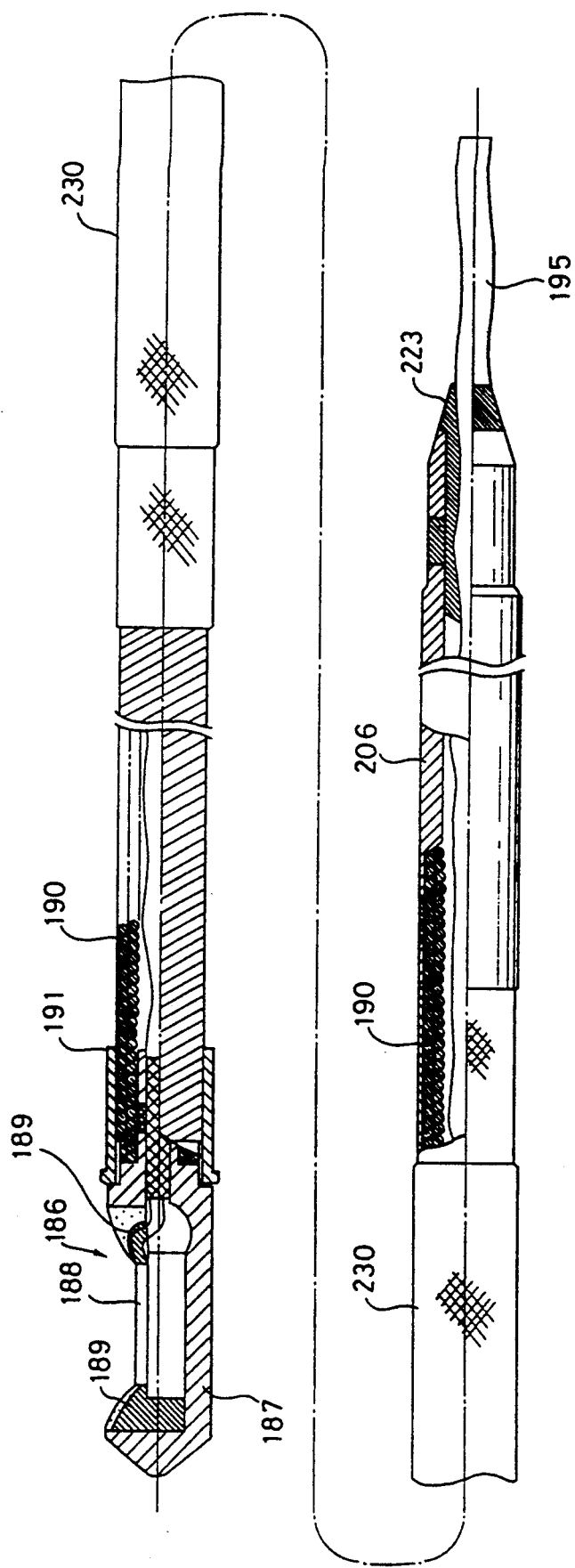
FIG. 15 is a sectional view showing an ultrasonic probe of the device according to the fifth embodiment of the present invention.

As shown in FIG. 15, the outer circumference of the drive shaft 190 is covered by the conductive braid 230 which comprises netting brands of material such as brass, which is low in electric resistance, like a cylinder. The drive shaft 190 is completely covered by the braid 230 in this case, leaving only its front end portion not covered. The front and rear ends of the braid 230 are fixed to the drive shaft 190 by soldering to make them electrically conductive. In short, the third conductive means is thus formed.

When the fifth embodiment of the present invention is to be used, the connecting connector 172 at the inserting section 170 is connected to the drive operating section 173. The rotation receiving pins 219 on the outer surface of the connector pipe 217 are this time engaged with rotation output terminals at the drive operating section 173. The rotation output terminals are connected to the drive shaft 190 via the connector pipe 217, the slider ring 214, the slider pin 212, the slider 211 and the metal fitting 206 at the connecting connector 172. Rotation force is transmitted to the ultrasonic wave transmitting and receiving section 186 at the front end of the drive shaft 190 through these components. Ultrasonic signals are transmitted to and received by the ultrasonic wave transmitting and receiving section 186 via the signal cable 195 to display ultrasonic images on the TV monitor 180 of the ultrasonic view means 174.

In the case of the fifth embodiment, the measure to shield noises outside includes the first conductive means which uses the external conductive line of the coaxial signal cable 195, the second conductive means formed by connecting the conductive probe holder 187 which holds the ultrasonic vibrator 188 to the common of the coaxial connector 222 via the drive shaft 190 connected to the probe holder 187 and housing the signal cable 195 therein, the metal fitting 206, the conductive bearing 207, the connector body 201 of the connecting body 202, the conductive bearing and slider ring 213 and 214, and the conductive connector pipe 217 so as to make the potential of the probe holder 187 located on the front side the same as that of the coaxial connector 222 located on the rear side, and the third conductive means formed by covering the outer circumference of the drive shaft 190 made of material such as phosphor bronze, relatively high in resistance, by the braid 230 which has good conductivity so as to make the whole of the means low in electric resistance. Excellent shield effect relative to noises can be achieved by the conductivity of these conductive means. When the drive shaft 190 is made of highly conductive material such as phosphor bronze lines or strands, its mechanical strength is reduced. When it is shaped like a coil, its impedance at high frequency is increased and its impedance is so that the left as it is, shield effect cannot be achieved so much. The drive shaft 190 is not covered by the braid 230 at the whole length thereof but leaves its front end portion uncovered, that is, that portion of the shaft 190 which extends 30 cm, for example, from the front end thereof is left uncovered. When the inserting section is inserted, as the endoscope, into the body cavity, therefore, the rotation of the drive shaft 190 cannot be disturbed even if the curving portion and the swelled forceps outlet portion of the endoscope are bent at a small curvature.

According to this fifth embodiment as described above, not only the external conductive line of the signal cable 195 but also the probe holder 187 which holds the ultrasonic vibrator 188 is electrically connected to the drive shaft 190 by laser welding and introduced to the drive operating section 173, so that shield effect can be enhanced. Further, the drive shaft 190 made of stainless steel is covered by the highly conductive braid 230 and they are rotated like a unit. This also enables the effect of shielding noises to be further enhanced.

Figure 16:
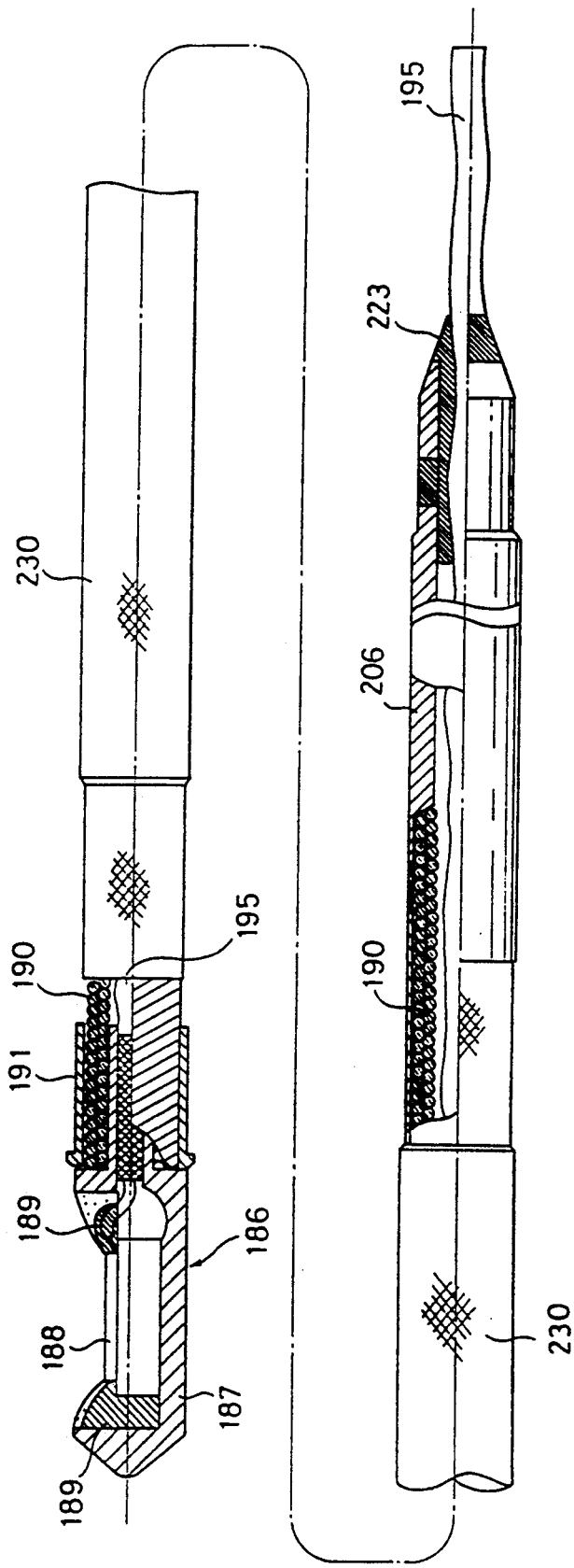
FIG. 16 is a sectional view showing the ultrasonic probe of the device for ultrasonically imaging and diagnosing a human body, which is realized as a sixth embodiment of the present invention.
Figure 17:
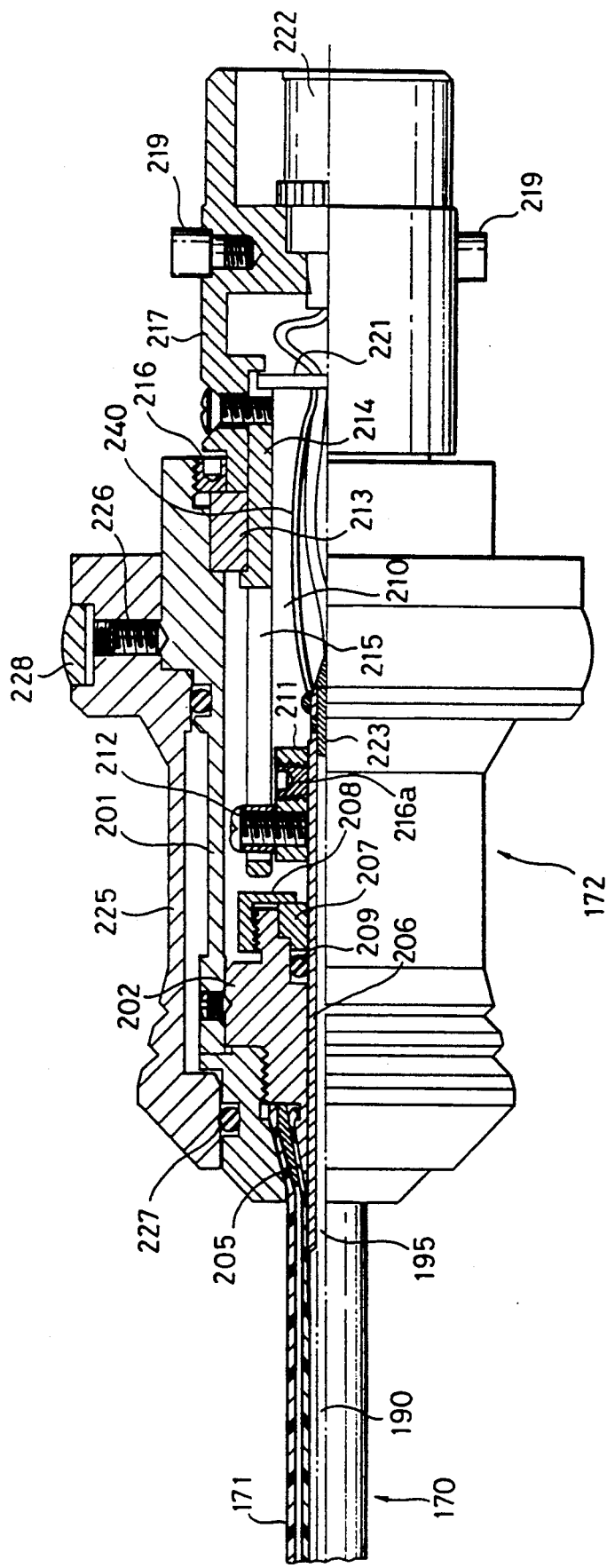
FIG. 17 is a vertically-sectioned view showing the connecting connector section in FIG. 16.

FIGS. 16 and 17 show a sixth embodiment of the present invention. The drive shaft 190 is covered by the braid 230 substantially at the whole length thereof in this case. As shown in FIG. 16, the covering of the braid 230 relative to the drive shaft 190 starts just behind the slide ring 191. Further, a cable 240 is connected, at one end thereof, to the metal fitting 206 which is electrically connected to the drive shaft 190 and the braid 230, and to the common of the base plate 221 at the other end thereof, as shown in FIG. 17. In short, the metal fitting 206 and the base plate 221 are connected directly to each other in this case. Therefore, noises shielding capacity can be made so high in this case.

The braid 230 may be made by strands of gold, tin-plated soft copper, beryllium tin copper or the like which is low in electric resistance, as well as by strands of brass.

Figure 18:
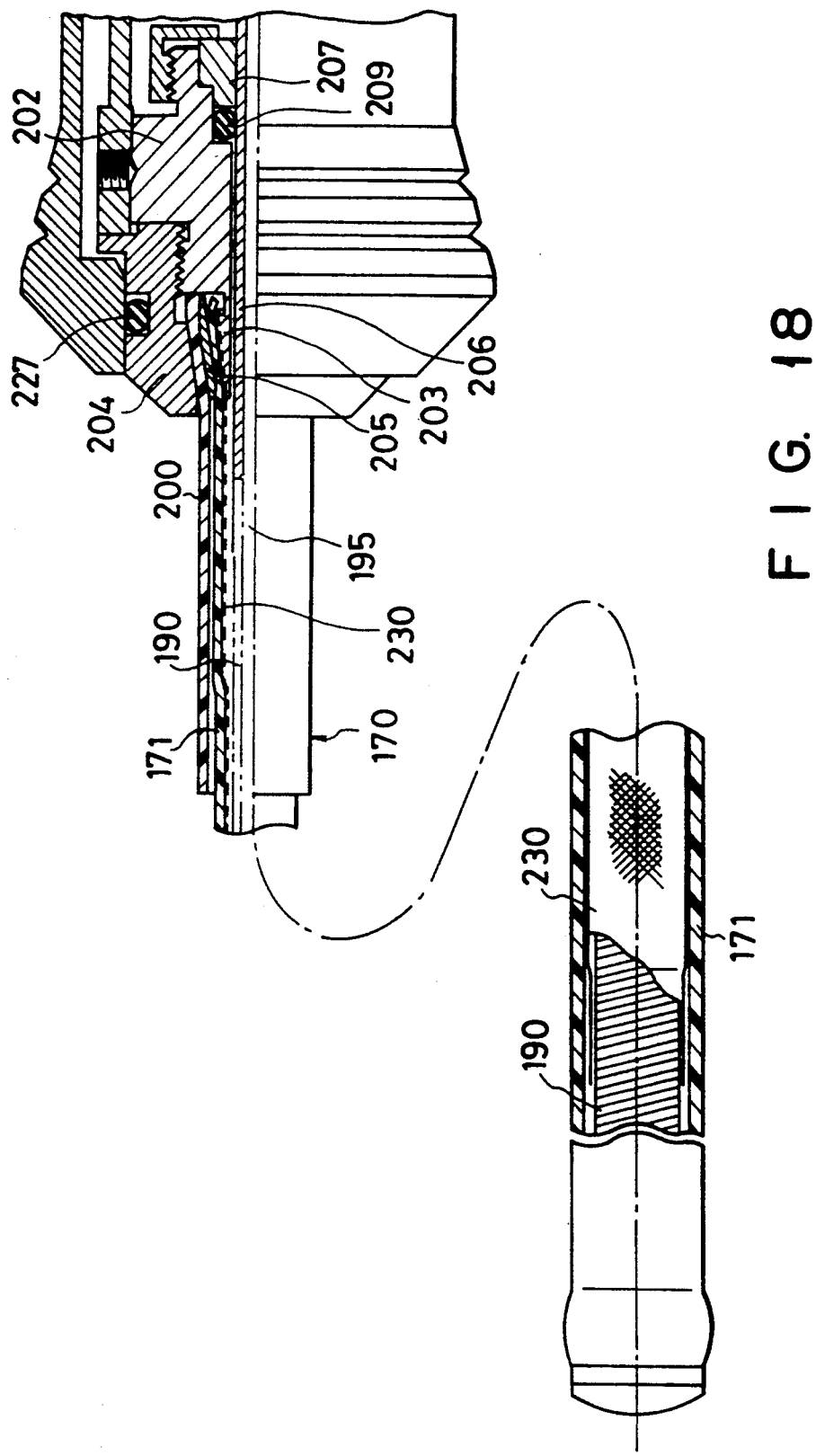
FIG. 18 is a partly-sectioned view showing an ultrasonic signals transmitting and receiving section of the device, which is realized as a seventh embodiment of the present invention.

FIG. 18 shows a seventh embodiment of the present invention.

In the case of this embodiment, the outer circumference of the drive shaft 190 is covered by the conductive braid 230 which is formed like a cylinder by netting strands of material such as brass, low in electric resistance, as shown in FIG. 18. Further, the braid 230 is located in the sheath 171 in such a way that the braid 230 completely covers the drive shaft 190 while leaving the front end portion of the shaft 190 uncovered and that it allows the drive shaft 190 to rotate in it. Its rear end is fixed to the tapered portion 203 of the connecting body 202 together with the sheath 171 and electrically connected there. The rear end and its vicinity of the sheath 171 are made larger in inner diameter so as not to interfere with the metal fitting 206. The front end of the braid 230 is made solid by solder so as not to become frayed. The third conductive means is thus formed.

In the case of this seventh embodiment, the measure to shield noises outside includes the first conductive means using the outer or external conductive line of the signal cable 195 which is of the coaxial type, the second conductive means formed by electrically connecting the conductive probe holder 187 which holds the ultrasonic vibrator 188 to the common of the coaxial connector 222 via the drive shaft 190 connected to the probe holder 187 and housing the signal cable 195 therein, the metal fitting 206, the conductive bearing 207 and the connecting body 202, and the third conductive means formed by locating the braid 230, good in conductivity, in the sheath 171 while covering the drive shaft 190, relatively high in resistance, to make electric resistance low as a whole through the connecting body 202. The effect of excellently shielding noises can be achieved due to the conductivity of these conductive means. When the drive shaft 190 is made by strands of material such as phosphor bronze which is good in conductivity, its mechanical strength is reduced. When it is shaped like a coil, its impedance is increased at high frequency and when its impedance is left as it is, noises shield effect cannot be enhanced so much. The braid 230 is located or housed in the sheath 171, not covering the whole length of the drive shaft 190 but leaving the front end portion of it uncovered, that is, that portion of it which extends 30 cm, for example, from its front end is left uncovered. When the inserting section is inserted into the body cavity as the endoscope, therefore, the rotation of the drive shaft 190 cannot be disturbed even if the curving portion and the swelled forceps outlet portion of the endoscope are curved at low curvature.

Further, the braid 230 is a member independent of the drive shaft 190. This can prevent the rotating capacity of the drive shaft 190 from being damaged.

According to the seventh embodiment as described above, not only the outer copper or conductive line of the signal cable 195 but also the probe holder holding the ultrasonic vibrator is electrically connected to the drive shaft 190 by soldering and introduced to the drive operating section to thereby enhance the noises shielding effect. Further, the good conductive braid 230 is arranged in the sheath 171, covering the drive shaft 190 made of stainless steel, and electrically connected to the connecting body 202. The effect of shielding noises can be thus further enhanced.

It may be arranged that the braid 230 is located in the sheath 171, not leaving the front end of the drive shaft 190 uncovered but covering the whole length of it.

FIG. 19 shows an eighth embodiment of the present invention. This embodiment is similar to the above-described ones except that the device is of the linear scan type wherein scanning is conducted while moving the drive shaft 190 forward and backward. According to the eighth embodiment, not only the signal cable 195 but also the drive shaft 190 and the good conductive braid 230 are used as the outer copper line. The common potential of the reception circuit can be made more stable to further enhance the noises shielding effect. In addition, the drive shaft 190 and the braid 230 are arranged to cover the signal cable. The effect of shielding noises can be thus still further enhanced.

It should be understood that the present invention is not limited to the above-described embodiments and their variations and various changes and modifications can be made without departing from the spirit and scope of the present invention.

What is claimed is:

1. An ultrasonic imaging device comprising:
   an inserting section adapted to be inserted into a body cavity, said inserting section having a front end;
   an ultrasonic wave transmitting and receiving section located at the front end of the inserting section;
   a conductive hollow shaft located at the inserting section and connected to the ultrasonic wave transmitting and receiving section;
   scanning means for scanning the body cavity while changing the direction of an ultrasonic wave transmitted from the ultrasonic wave transmitting and receiving section;
   circuit means for receiving electric signals applied from the ultrasonic wave transmitting and receiving section, said electric signals corresponding to an image of a scanned portion of the body cavity, said circuit means having a common;
   a signal cable guided through the hollow shaft to connect the ultrasonic wave transmitting and receiving section to the circuit means;
   first means for preventing noise from entering into the signal cable, said first means including an outer conductive line of the signal cable connected to the circuit means;
   second means for preventing noise from entering into the signal cable, said second means including the hollow shaft connected to the common of the circuit means; and
   third means for preventing noise from entering into the signal cable, said third means surrounding the signal cable and having a conductive member connected to the common of the circuit means.

2. The device according to claim 1, wherein said scanning means includes drive means for mechanically moving the ultrasonic wave transmitting and receiving section through the hollow shaft.

3. The device according to claim 2, wherein said drive means includes means for moving the ultrasonic wave transmitting and receiving section in the radial direction.

4. The device according to claim 2, wherein said drive means includes means for moving the ultrasonic wave transmitting and receiving section in the linear direction.

5. The device according to claim 2, wherein said drive means includes means for moving the ultrasonic wave transmitting and receiving section like a sector.

6. The device according to claim 1, wherein said hollow shaft is flexible.

7. The device according to claim 1, wherein said conductive member has a base end connected to the common of the circuit means and a front end connected to the common of the ultrasonic wave transmitting and receiving section.

8. The device according to claim 1, wherein said conductive member has a base end connected to the common of the circuit means and a front end located remote from the ultrasonic wave transmitting and receiving section.

9. The device according to claim 1, wherein said third means has a conductive line for electrically connecting the conductive member to the common of the circuit means.

10. The device according to claim 1, wherein said conductive member has a conductive braid enclosing the signal cable.

11. The device according to claim 1, wherein said conductive member has metal-made braid arranged around the inserting section.

12. The device according to claim 1, wherein said third means has a conductive housing which forms the front end of the inserting section, and a slide bearing by which the hollow shaft is supported relative to the housing and through which the housing is electrically connected to the hollow shaft.

13. The device according to claim 1, wherein said third means includes a conductive housing which forms the front end of the inserting section, and a conductive shield member electrically connected to the housing and enclosing the hollow shaft.

14. The device according to claim 1, wherein said third means includes a conductive housing which forms the front end of the inserting section, and a metal braid arranged around the inserting section and electrically connected to the housing.

15. The device according to claim 1, wherein said third means has a conductive housing which forms the front end of the inserting section, and a conductive O-ring for electrically connecting the housing to the hollow shaft.

16. The device according to claim 15, wherein said third means has either of a conductive shield member electrically connected to the housing and enclosing the hollow shaft, and a metal-made braid arranging around the inserting section and electrically connected to the housing.

17. The device according to claim 1, wherein said third means has a conductive housing which forms the front end of the inserting section, a slip ring attached to the hollow shaft, and a brush arranged in the housing to contact the slip ring, said slip ring and brush serving to connect the housing to the hollow shaft.

18. The device according to claim 17, wherein said third means has either of a conductive shield member electrically connected to the housing and enclosing the hollow shaft, and a metal-made braid arranged around the inserting section and electrically connected to the housing.

19. The device according to claim 1, further comprising an endoscope provided with a casing in which the circuit means is housed, and a rotation driving system for rotatably driving the ultrasonic wave transmitting and receiving section, wherein said first, second and third means are connected to the common of the circuit means through the casing of the endoscope and the rotation driving system.

20. The device according to claim 1, wherein said signal cable is of a coaxial type having a core line and an outer conductive line, said ultrasonic wave transmitting and receiving section has an anode and a cathode, the core line of said signal cable is connected to the anode of said ultrasonic wave transmitting and receiving section, and the outer conductive line thereof is connected to the cathode of the ultrasonic wave transmitting and receiving section to form the first means.

21. The device according to claim 1, further comprising ultrasonic images viewing means connected to the circuit means, wherein said viewing means has an earth line to which the common of the circuit means is connected.

* * * * *